United States Patent [19]

Horng

[11] Patent Number: 5,068,421

[45] Date of Patent: Nov. 26, 1991

[54] CHEMICAL PROCESS

[75] Inventor: Liou-Liang Horng, Creve Coeur, Mo.

[73] Assignee: Monsanto Company, St. Louis, Mo.

[21] Appl. No.: 585,541

[22] Filed: Sep. 20, 1990

Related U.S. Application Data

[63] Continuation-in-part of Ser. No. 235,854, Aug. 24, 1988, Pat. No. 4,959,496.

[51] Int. Cl.$^5$ .......................................... C07C 59/125
[52] U.S. Cl. .................................................. 562/583
[58] Field of Search ......................................... 562/583

[56] References Cited

U.S. PATENT DOCUMENTS

| | | | |
|---|---|---|---|
| 3,635,830 | 1/1972 | Lamberti et al. | 252/152 |
| 3,692,685 | 9/1972 | Lamberti et al. | 252/89 |
| 3,914,297 | 10/1975 | Lamberti et al. | 260/535 |
| 4,663,071 | 5/1987 | Bush et al. | 252/174.19 |
| 4,689,167 | 8/1987 | Collins et al. | 252/95 |
| 4,798,907 | 1/1989 | MacBrair et al. | 562/580 |
| 4,867,901 | 9/1989 | Bosch et al. | 562/583 |
| 4,904,824 | 2/1990 | Horng et al. | 562/583 |
| 4,950,787 | 8/1990 | Griffith et al. | 562/583 |
| 5,001,245 | 3/1991 | Nakano et al. | 562/583 |

FOREIGN PATENT DOCUMENTS

| | | | |
|---|---|---|---|
| 0320213 | 6/1989 | European Pat. Off. | 562/583 |
| 0328153 | 8/1989 | European Pat. Off. | 562/583 |

OTHER PUBLICATIONS

Chemical Abstracts, vol. 60, 2295g, 1964.
Chemical Abstracts, vol. 64, 4224g, 1966.

*Primary Examiner*—Bruce Gray
*Attorney, Agent, or Firm*—Raymond C. Loyer; Richard H. Shear; James C. Bolding

[57] ABSTRACT

There is disclosed herein improved processes for the preparation of ether carboxylates by reacting in an alkaline reaction medium the salts of maleic acid and malic acid in the presence of a calcium ion catalyst wherein unreacted acid salts are recovered from the reaction medium by lowering the pH of the reaction medium to a range of from about 4 to about 6 in two steps, the first step ending at a pH in the range of from about 7 to about 8.5. The precipitate is removed and the pH of the reaction medium is then lowered further to a pH in the range of 4 to 6. The precipitated salts are recycled to the synthesis reaction to prepared additional amounts of product.

14 Claims, No Drawings

CHEMICAL PROCESS

This application is a continuation-in-part of copending application Ser. No. 235,854 filed Aug. 24, 1988, now U.S. Pat. No. 4,959,496.

This invention relates to a process for making ether carboxylic acids and more particularly to processes for making ether carboxylates prepared by a calcium ion catalyzed reaction in alkaline medium of maleic and malic acid salts. Such reactions are of the type typically referred to as Michael condensation reactions.

Polycarboxylic acids have long been known to be useful, usually in the salt form, as detergent builders or sequestrants. Also, ether carboxylates useful as metal sequestering and detergent builders have been known and are most desirable for their beneficial effects in laundering applications.

Because ether carboxylates have such effective sequestering ability they have become attractive in recent times for the replacement of sodium tripolyphosphate which has long been the leading detergent builder or sequesterant. Examples of prior art efforts to provide ether carboxylate detergent builders or sequesterants are found in U.S. Pat. Nos. 3,635,830; 3,692,685 which relate to the use of oxydisuccinic acid salts particularly 2,2'-oxydisuccinate salts (ODS) as detergent builders. Another example of an ether polycarboxylate detergent builder or sequesterant is found in U.S. Pat. No. 3,914,927 which relates to carboxymethyl oxysuccinates.

While many carboxylate compounds in the prior art have utility as a builder or sequesterant in laundry detergent formulations, it has been found that certain ether carboxylates are more attractive and cost effective for such utility. In the field of detergent builders and sequesterants for laundry detergent formulations low cost of the components is extremely important because it is in a very competitive market. While many ether carboxylate compounds have been found to be useful there is needed more economical manufacturing processes whereby such compounds can be economically produced in large volume.

One example of ether carboxylates is a mixture of polycarboxylic acids or salts thereof, particularly the sodium salts, of 1-hydroxy-3-oxa-1,2,4,5-pentane tetracarboxylic acid (HOPTC) and 3,6-dioxa-1,2,4,5,7,8-octane hexacarboxylic acid (DOOHC) which is highly useful in detergent formulations as a sequesterant or builder. This mixture is prepared by reaction of a combination of D,L-tartrate salts with maleate salts catalyzed by calcium ions. Due to equilibria present in the reaction and to the need for the presence of particular reactant ratios to obtain particularly preferred ratios of HOPTC and DOOHC in the product, there is considerable unreacted D,L-tartrate and maleate present at the end of the condensation reaction. Further, to provide a more economical process it is desired that a means be found to economically recover and reuse the unreacted D,L-tartrate and maleate rather than merely discharging maleate and tartrate as waste.

The synthesis of many ether carboxylates, including the mixture of HOPTC and DOOHC as well as the oxydisuccinates is achieved in an equilibrium reaction wherein starting materials, tartrate or malate and maleate salts, remain in solution at the end of the reaction. In many cases these starting materials are removed only by solvent extraction which is expensive and not ecologically attractive. Large scale production of such ether carboxylates incur large costs for recovery of reactants and an ecologically and environmentally acceptable means for recovering unreacted starting material is practically a requirement for industrial production of commercial quantities of these ether carboxylates.

There has previously been discovered a process for preparing ether carboxylates by the reaction of the salts of malic acid and maleic acid, said reaction catalyzed by calcium ions and conducted under alkaline conditions wherein unreacted salts are conveniently recovered in such manner that they may be recycled to the synthesis reaction to produce additional ether carboxylate. It was discovered that at a limited range of acidity certain unreacted salts are conveniently recovered from the reaction mixture at the conclusion of the reaction. By reducing the pH of the reaction mixture to a range within about 4 to about 6 by combining a suitable acid with the reaction mixture, the insoluble salts of starting acids precipitate while the desired ether carboxylate product remains in solution. The precipitate is removed by known means such as filtration thereby allowing further processing of the ether carboxylate solution. Such further processing will depend, of course, upon the particular ether carboxylate produced.

SUMMARY OF THE INVENTION

It has now been discovered that an increased amount of unreacted malate salts are recovered by reducing the pH of the alkaline, calcium catalyzed reaction mixture of maleic and malic acids salts in two steps, to the final pH of from about 4 to about 6. In the first step the pH is reduced to a range of from about 7 to about 8.5 whereby the a majority of the malate salts precipitate and are removed by conventional means. After removal of the precipitated malate salts, the pH of the remainder of the reaction mixture is reduced further to a pH in the range of from about 4 to about 6, preferably about 5. In accordance with the above procedure an increased amount of the malate salts are removed from the reaction mixture and made available for recycle for the preparation the additional amounts of the desired oxydisuccinic acid salts.

In another aspect of this invention, the calcium ions employed to catalyze the condensation reaction to prepare the ether carboxylate is conveniently recovered and recycled to the synthesis reaction by precipitating the calcium as a calcium carbonate. The precipitation is accomplished by combining the reaction mixture, typically after removal of unreacted starting salts, with an alkaline earth or alkali metal carbonate at a pH in the range of from about 7 to about 12. The precipitate is removed by known means, preferably by filtration or centrifugation.

DETAILED DESCRIPTION OF THE INVENTION

Calcium catalyzed reactions for the production of ether carboxylates are known. A typical example of such a process is disclosed in U.S. Pat. No. 4,663,071 to Bush et al and such patent is hereby incorporated by reference. Another example of a process for preparing ether carboxylates in the presence of calcium ions is EPO 0 236 007A also to Bush et al which publication is also incorporated herein by reference.

It is typical of the Michael condensation reactions to provide the most effective equilibrium state for the production of the desired compound or mixture by control of the reactant ratio. For example, high ratios of maleic acid salts to malate acid salt in the range of 2 to 1 or greater respectively provide the more optimum production of ODS in the calcium ion catalyzed reaction disclosed in the European publication referred to above. However, a significant amount of unreacted maleate salt remains in solution at the end of the reaction together with the desired ODS.

The recovery of unreacted maleate salts from calcium catalyzed reactions of maleic acid salts with salt of malic acid in alkaline medium is conveniently achieved by acidifying the reaction product so as to reduce the pH to within the range of about 4 to about 6. However it has been found that the salts of malic acid in the reaction mixture are least soluble at a pH in the range of from about 7 to about 8.5 and such salts become increasingly soluble as the pH is reduced further to the above mentioned range of from about 4 to about 6. Preferably, the acid addition to the reaction mixture is interrupted when the pH of the reaction mixture reaches slightly below 8. The precipitated salts are then removed before reducing the pH to the desired lower level of from about 4 to about 6. The lower range is optimum for precipitation and removal of the maleic acid salts in the form of sodium hydrogen maleate. The lower pH range also provides removal of a majority of the malic acid salts but it has now been discovered that the malic acid salts which have precipitated during acid addition for the purpose of lowering the pH to a range between about 4 and about 6 begin to redissolve into the reaction mixture before completion of the process of acid addition and removal of the precipitate. To remove the maximum amount of malic acid salts it is necessary to interrupt acid addition at the higher pH range and remove precipitated acid salts. Even though malic salts are removed at the higher pH range, it has been found that the precipitation and removal of further amounts of malic acid salts still occurs together with the precipitation of the sodium hydrogen maleate salt at the lower pH range of from about 4 to about 6.

A particular advantage of the process of this invention, whereby unreacted maleate salt is recovered, is the ability to regulate the reactant ratios more freely since convenient recovery and recycle is possible. Loss of unreacted maleate salt is insignificant and its recovery economical, particularly when maleic acid is employed to reduce the pH of the reaction product of the condensation reaction. High maleate to malate ratios such as in excess of 1 to 1 respectively have been found to result in the reduction or even elimination of the maturation step usually required in the production of ODS. Therefore, a preferred embodiment of this invention is the calcium catalyzed reaction of maleate and malate salts in alkaline medium wherein the ratio of maleate to malate salt is in excess of 1.

It has been found that the small amounts of by-products such as fumarate and residual amounts of ODS trapped in the precipitate are not deleterious to the use of this recycled precipitate in subsequent condensation synthesis reaction.

FORMATION OF ODS

As noted above there has been previously disclosed an ether-bond forming reaction using the combination of sodium and calcium salts in aqueous alkaline ether-bond forming reactions to provide in high yield ether carboxylates. One such disclosure is EPO 0 236 007. The ether carboxylate is formed in a reaction mixture containing sodium and calcium salts of maleic acid and malic acid which react to form the sodium and calcium salts of ODS. The reaction takes place at temperatures below about 120° C. in aqueous medium wherein one component is the maleate salt and the other is the malate salt. The reaction mixture also contains an inorganic reactant component consisting essentially of at least one inorganic base or mixture thereof. The reaction mixture is held at a temperature of at least about 60° C. for a period sufficient to permit a major portion of the ether-bond formation between the maleate and malate present in the reaction mixture. According to previously known reactions the malate to maleate molar ratios range from about 1:1 to about 2:1, more preferably from about 1.1:1 to about 1.6:1 at the initial time of combination.

The molar ratio of calcium to maleate plus malate is disclosed in the prior art to be in the range of from about 0.1:1 to about 0.75:1, more preferably from about 0.31:1 to about 0.57:1. Also present in the reaction mixture is sodium which is present at a molar ratio of sodium to maleate plus malate of from about 0.5:1 to about 2.2:1. Ratios of sodium to malate and maleate are adjusted in the event the acid form of these compounds are employed and no organic salts are used. When the acid form of maleate and malate are employed the sodium to maleate plus malate molar ratio is generally in the range of from about 0.9:1 to about 1.48:1. As noted above, the reaction mixture is alkaline generally by the addition of an inorganic base so as to provide from about 0.01 to about 0.4 moles of free hydroxide per mole of combined maleate and malate. Preferably the free hydroxide is present in the range from about 0.04:1 to about 0.2:1 per mole of combined maleate and malate, preferably from 0.04:1 to 0.1:1 respectively. The reaction is reported to have been performed at a pH in the range of from about 9 to about 13 measured by cooling the reaction mixture sample to 25° C. and diluting to about 5% dissolved solids prior to pH measurement.

In accordance with this invention the malate/maleate ratio is reversed such that it is now convenient and economical to operate the reaction to produce ODS with an excess of maleate in the reaction mixture. In general the malate to maleate molar ratios in accordance with the process of this invention can range from about 1:1.5 to 1:3 respectively or even higher. Of course, the excess maleate does not react but is recovered in accordance with this invention for reuse in a convenient manner as will be more fully described below. Calcium hydroxide level is typically in the range of, on a molar basis of malate to calcium hydroxide, from 1:1 to 1:2. Calcium levels affect the reaction rate but have little effect on the ability to recover unreacted starting material in the form of sodium hydrogen maleate. An excess of base has been discovered to increase the speed of the reaction but also it increases the speed of the reversion of the desired ODS product to fumarate. In general, the reactant ratios in the reaction mixture in accordance with this invention in terms of malic acid/ maleic acid/calcium hydroxide/sodium hydroxide mole ratio is typically in the range of 1/2.2/1.6/3.4. These ratios are the usual mid-point of ranges commonly employed and found to provide optimum results in accordance with this invention and can vary widely.

The reaction temperature of the process of this invention appears to control the rate of reaction and thus the amount of time required to produce optimum results. Typically, at 80° C. the reaction proceeds to completion in from about 1 to 3 hours for maximum malate conversion utilizing the above-mentioned reactant ratios. When the reaction is run at about 70° C. maximum malate conversion occurs in from 2 to 6 hours and such conversion is slightly higher than is found at a reaction temperature of 80° C. Acceptable results have been obtained at higher temperatures (90°/100° C.) with reaction times of 1 hour or less; however, the amount of fumarate formed increases rapidly.

The aqueous reaction mixtures forming ether carboxylates by the reaction of maleate and malate according to prior art methods contain from about 31% to about 41% by weight, more preferably 36% to about 40% by weight maleate and malate. The reaction mixture in accordance with this invention may contain from about 40% to 75%, by weight of the maleate and maleate salts. The progress of the reaction is typically determined by applying techniques such as High Performance Liquid Chromatography (HPLC) whereby the yield of ODS and the levels of maleate and malate reactants and of fumarate by-products and other individual reaction product can be monitored. The reaction is terminated by cooling typically to below 50° C. and preferably to ambient temperature. In prior art reactions, yields of at least 50% of the ODS based upon malate were obtained. However, in accordance with the process of the present invention the yields can be higher and product processing shorter due to adjustment of reactant ratios and to the convenient recovery of unreacted starting materials. Because starting materials are conveniently recovered, greater freedom of reactant ratios in the initial reaction mixture are obtained to the benefit of greater conversion and shorter processing time to provide a final product. It is reported that the complex sodium/calcium salts of the maleate and malate reactants as well as the ODS product formed in situ provide much higher solubilities of the reaction product than when single-metal calcium salts are employed. Such solubility is advantageous because it allows convenient high-concentration processes, easier pumping and handling properties.

In accordance with this invention monosodium maleate is easily recovered from the reaction product by reducing the pH of the reaction product to a range of from about 4 to about 6 whereby the unreacted starting material precipitates as monosodium maleate and is easily recovered for recycle to the synthesis reaction. Such process will be more fully described below.

The reaction mixture containing mixed salts of ether carboxylates also contains relatively large amounts of unreacted maleic acid salt. Maleic acid, in the monosodium salt form, is recovered and recycled to provide higher efficiency of utilization of this valuable raw material.

The recovery of maleate and malic salt is achieved by lowering the pH of the reaction mixture whereby sodium hydrogen maleate or monosodium maleate precipitates. In the preferred embodiment the reaction mixture is also cooled and diluted with water. An acidic material such as sulfuric acid, or an organic acid such as formic acid is added in sufficient amount to bring the combined synthesis mass and acid to a final pH in the range of from about 4.5 to 5.5, preferably slightly below 5.2. Any number of acidic materials can be employed to lower the pH of the reaction mixture. Combinations of acidic materials may also be employed. Typical examples of such acids are sulfuric acid, hydrochloric acid, nitric acid, formic, acetic, propionic, butyric and D,L-tartaric, carbonic, phosphoric, sulfonic, sulfurous, boric, phosphorous, adipic, benzoic, citric, fumaric, glycolic, malic, maleic, malonic, oxalic, succinic, sorbic, nitrilotriacetic, long chain fatty acids, etc.

In the process of this invention, the acid substance may be added to the crude reaction mass. Alternately, the reaction mass may be added to a heel containing the acid substance. In a further process of this invention, the acid substance and the reaction mass may be added concurrently into a mixing vessel. Sufficient water is added to the reaction mass and/or acid material so that the final concentration of desired ether carboxylate in the completed mixture is from about 40% to about 55%, by weight.

Sufficient acids are added to reach the preferred pH range of from about 4.5 to about 5.5 and the precipitated reaction mass is cooled to below 50° C. Preferably the reaction mass is cooled to a range of from just above the freezing point of the mixture to about 40° C., most practically to about 20° C. to about 30° C. Satisfactory filtration rates are thus obtained in large scale production. In a preferred mode, cooling the reaction product from the 80° C. reaction temperature to 65° C. over 30 minutes is followed by slow cooling to from about 30° C. to about 40° C. The suspension is then allowed to rest for about 30 minutes. The slurry is preferably cooled slowly with mild or slow agitation so as to grow particles which can be filtered in an appropriately short time. Other methods of acid addition such as are noted above can also be employed with appropriate adjustment of precipitation conditions.

When a mixed acid solution is employed to precipitate maleate and malic salts in the process of this invention, the acids may be added either sequentially or concurrently. In one mode of operation, the reaction mass at a temperature of about 80° C., is added to a heel of aqueous acid, typically formic acid, and then a solution of maleic acid is added to the partly neutralized reaction mass.

Removal of the precipitated acid salt may take any form practical and typically is performed by continuously drawing the slurry from the precipitator to a belt or drum filter or centrifuge. Other forms of removal such as decantation, etc. may also be employed. The filtrate contains the ether carboxylate in salt form. In a preferred embodiment the filtrate is transferred to another precipitator for removal of the calcium cations in the form of calcium carbonate.

Throughout pH reduction, cooling is required to maintain the temperature of the reaction mixture in the desired range of about 35° C. As noted above, the reaction mixture is held for about 30 to about 40 minutes after final pH reduction to allow crystal formation. The larger agglomerates are more easily separated from the reaction mixture.

In the production of ODS the filter cake containing mostly monosodium maleate is discharged and in one embodiment reslurried with water. The slurry is recycled directly or indirectly to the synthesis reaction. In a preferred embodiment the maleate salt is mixed with calcium obtained from the calcium carbonate recovered as described below.

CALCIUM CARBONATE PRECIPITATION

After removal of the insoluble acid salt or salts as described above, the filtrate from such operation is recovered and purified for use as detergent builder. In a preferred embodiment, calcium is removed either batchwise or preferably continuously. Typically, the filtrate from the above-mentioned step is pH adjusted with a base, preferably sodium hydroxide, as it is being fed into a calcium carbonate precipitator to bring the pH of the solution into a range of from about 10 to about 12, preferably from about 10 to about 10.5. The pH adjustment may be performed either in the precipitator or in a separate vessel if desired. The pH adjusted material is maintained in the range of from about 75° C. to about 110° C., preferably at about 90° C. to 100° C. Concurrently a solution of a basic carbonate, preferably sodium carbonate, preferably at a concentration of about 25%, is added to the precipitator to provide an overall mole ratio of carbonate to calcium of 1.3:1.

Alternatively, calcium carbonate is removed by increasing the mole ratio of carbonate ion to calcium ion without change in pH.

Although this invention is described with respect to carbonate precipitation using the preferred sodium cation, it is to be understood that other suitable cations may also be employed to obtain precipitation of calcium carbonate. Other cations useful in the process of this invention include potassium, ammonium and organo substituted ammonium. Other salts may be employed to obtain the calcium carbonate precipitate and includes sodium bicarbonate and mixtures of carbonates and bicarbonates.

During the precipitation of calcium carbonate it is preferred that water is continuously removed from the slurry to maintain the concentration of the organic acid salts in the range of from about 30% to about 50% by weight. Filtration of the precipitated calcium carbonate may take any form practical and typically is performed by continuously drawing the slurry from the precipitator to a centrifuge or to a belt or drum filter. The filtrate contains the desired ether carboxylate mostly as the alkaline salt along with minor amounts of raw material and by-products.

The wet cake from the separation is mechanically reslurried with water to form an approximately 50% calcium carbonate slurry for recycle to the synthesis reaction. The recovered carbonate may be added directly to the ether carboxylate synthesis reactor or together with recovered, unreacted tartrate and maleate. Preferably, the recovered calcium carbonate is converted to calcium maleate in a separate vessel before return to the synthesis reaction.

CALCIUM MALEATE FORMATION

Before introduction into the synthesis reaction, the calcium carbonate precipitate obtained from the product as described above is preferably converted to calcium maleate by reaction with maleic acid and/or sodium hydrogen maleate recovered from prior reactions in the production of ODS. Preferably, the maleic acid is prepared in situ. In one embodiment, the maleic acid is prepared by charging molten maleic anhydride to water heated to 65° C. to 75° C. After hydrolysis of the maleic anhydride to maleic acid is complete, the slurry of calcium carbonate solids is added at a rate slow enough to avoid uncontrolled foaming due to the evolution of carbon dioxide. During the addition of calcium carbonate the reaction mass is heated to a temperature in the range of from about 90° C. to about 100° C. and preferably to about 95° C.

Although the above described process follows a particular scheme, it is obvious that other schemes or flow charts may also be followed. For example, hold tanks, mixing tanks and transfer tanks may be employed which are not described above. Other variations will occur to those knowledgeable in the art.

To further illustrate the process of the present invention there is described below non-limiting preferred embodiments. In the following examples the solution obtained from the removal of calcium carbonate may be further purified such as by methanol extraction to provide a material useful as a detergent builder.

EXAMPLE 1

To a one liter Ace reactor, there were added 300 grams of water followed by the addition of 196 grams of maleic anhydride followed by the addition of 160 grams of calcium carbonate and 310 grams of additional water. After thoroughly mixing the above materials there were added 134 grams of DL malic acid followed by the addition of 175 grams of 50% aqueous sodium hydroxide. After again thoroughly mixing the materials added to the reactor, 260 grams of water were removed by boiling. After water removal 65 grams of a 50% aqueous solution of sodium hydroxide was added and the temperature reduced to 70° C. During the reaction removal of water was continued by vacuum evaporation until the solids concentration in the reaction mixture reached about 60%, by weight. The reactor was maintained at a temperature of 70° C. for 7 hours. At the end of 7 hours the reaction mixture was quenched by the addition of 150 grams of water and the reaction mass cooled to 30° C. To the cooled reaction mass were added sufficient formic acid to reduce the pH to about 5.05. Both malate and sodium acid maleate precipitated from solution. The suspended solid solution was filtered and washed with water. The composition of the filter cake and filtrate were analyzed and the analysis is presented below in Table I as weight percent.

TABLE I

|  | Filter Cake | Filtrate |
|---|---|---|
| Malate | 7.495 | 5.187 |
| Maleate | 28.598 | 0.468 |
| ODS | 6.992 | 24.515 |
| Fumarate | 0.135 | 0.27 |

Subsequent investigation has determined that only about 50% to 60% of the malate salt was recovered in the filter cake. The remainder was lost because of its solubility at the pH of about 5.

EXAMPLE 2

The procedure of Example 1 was repeated with the exception that the reaction mass was cooled to about 35° C. when formic acid was added to reduce the pH to a level of about 7.7. Both sodium hydrogen maleate and malate salts precipitated out and were filtered from the reaction mass. An analysis of the filtrate and filter cake were made and are presented below in Table II wherein all of the results are presented in weight percent.

TABLE II

|  | Filter Cake | Filtrate |
|---|---|---|
| Malate | 13.098 | 4.173 |
| Maleate | 27.344 | 11.315 |
| ODS | 13.525 | 23.097 |
| Fumarate | 0.188 | 0.303 |

The results of the analysis indicates that from about 75% to about 85%, by weight, of the malate salts and about 65% to about 75%, by weight, of the maleate salts have precipitated from solution. Formic acid was then added to the filtrate in sufficient amounts to reduce the pH to about 5.1. Both sodium hydrogen maleate and malate salts precipitated. The salts were removed from the reaction mass by filtration. Both the filter cake and the remaining filtrate were analyzed and the results of the analysis are presented below in Table III wherein the results are presented in weight percent.

TABLE III

|  | Filter Cake | Filtrate |
|---|---|---|
| Malate | 6.653 | 5.375 |
| Maleate | 26.784 | 0.182 |
| ODS 1 | 2.787 | 6.086 |
| ODS 2 | 14.02 | 26.409 |
| Fumarate | 0.101 | 0.109 |

The above analysis indicates that from about 50% to about 60% of the remaining malate salts have been separated from solution in the filter cake and about 99% of the sodium hydrogen maleate in the filtrate has been separated from the solution.

There has been described an improved process for the production of ODS. The efficiency of the process is greatly improved by the greater removal of malate salts while the purity of the final product has also been improved.

While the process has been described above with reference to specific compounds and examples no intention is made by such reference to limit the scope of this invention unless expressly stated. Various modifications may be made in the materials and sequence of process steps without departing from this invention.

I claim:

1. An improved process for preparing the alkali metal salts of oxydisuccinic acid which comprises reacting in an alkaline reaction medium the salts of maleic acid and malic acid in the presence of calcium ion catalyst, reducing the pH of the reaction product to a range of from about 7 to about 8.5 whereby unreacted starting acids salts are precipitated and removed from the reaction product and then lowering the pH of the reaction product to a range of from about 4 to about 6 whereby additional starting acid salts precipitate and are removed from the reaction product.

2. A process of claim 1 wherein the pH is reduced by combining the reaction product with an organic acid.

3. A process of claim 2 wherein the organic acid is selected from the group consisting of formic, acetic, propionic, citric, maleic, tartaric, fumaric, malic, malonic, succinic, adipic, butyric and long chain fatty acids.

4. A process of claim 1 wherein the pH is reduced by combining the reaction product with an inorganic acid.

5. A process of claim 4 wherein the inorganic acid is selected from the group consisting of sulfuric, hydrochloric, carbonic, nitric, phosphoric, phosphorous, sulfonic and sulfurous acids.

6. A process of claim 1 wherein the pH is reduced by combining the reaction product with a mixture of organic and inorganic acid.

7. A process of claim 6 wherein the acids are sulfuric and maleic acids.

8. A process of claim 1 wherein the pH is reduced by adding the reaction product to an acid heel.

9. A process of claim 8 wherein acid heel contains a mixture of two acids.

10. A process of claim 9 wherein the acids in the heel are formic and maleic.

11. A process for preparing of the alkali metal salt of oxydisuccinic acid which comprises the steps of:
(a) forming an aqueous reaction mixture comprising from about 20% to 75% by weight of both calcium and monovalent cation salts of maleic acid and malic acid, said mixture corresponding to the overneutralized mixture which is formed by combining:
  (i) maleic and malic acid salts in a maleic to malic molar ratio of from about 1.1:1 to about 3:1;
  (ii) a source of calcium cations in an amount such that the molar ratio of malate to calcium hydroxide ranges from about 1:0.5 to 1:2 with the ratio of moles of calcium to total moles of maleic and malic acid being less than 1; and
  (iii) a neutralizing agent comprising a hydroxide of a monovalent cation in an amount to provide from about 0.01 to about 0.4 moles of free hydroxide per mole of combined maleate and maleate salts;
(b) maintaining said aqueous reaction mixture at a temperature of from about 50° C. to 120° C. for a time period sufficient to form a oxydisuccinic acid salts;
(c) lowering the pH of reaction mixture of step (b) to the range of from about 7 to about 8.5 and cooling the mixture to precipitate malate and monosodium maleate;
(d) removing the precipitate formed in step (c) from the reaction mixture and then lowering the pH of the remaining reaction mixture to a pH in the range of from about 4 to about 6;
(e) removing the precipitate formed in step (d) from the reaction mixture and combining it with the precipitate formed in step (c) and recycling it to step (a) to prepare additional amounts of reaction product;
(f) treating the reaction mixture from step (e) with a carbonate or bicarbonate whereby calcium carbonate precipitates;
(g) removing the calcium carbonate from the reaction mixture of step (f) and recycling it to step (a) to prepare additional amounts of reaction product; and
(h) recovering the reaction mixture from step (g).

12. A process of claim 11 wherein the carbonate is an alkali metal carbonate.

13. A process of claim 12 wherein the alkali metal is sodium.

14. A process of claim 11 wherein the bicarbonate is sodium bicarbonate.

* * * * *